United States Patent [19]

Allard et al.

[11] Patent Number: 5,116,385
[45] Date of Patent: May 26, 1992

[54] MEDIO-LATERAL CONTROL ENHANCING, CANTILEVER-SPRING TYPE PROSTHETIC FOOT

[75] Inventors: Paul Allard, Pierrefonds; Claude Levesque, Montréal; Jean Dansereau, Sainte-Thérèse, all of Canada

[73] Assignee: Universite de Montréal, Montreal, Canada

[21] Appl. No.: 695,918

[22] Filed: May 6, 1991

[51] Int. Cl.$^5$ ............................................. A61F 2/66
[52] U.S. Cl. ....................................... 623/55; 623/53
[58] Field of Search ................................ 623/53-56, 623/27

[56] References Cited

U.S. PATENT DOCUMENTS

| | | |
|---|---|---|
| 344,154 | 6/1886 | Bartlette . |
| 456,206 | 7/1891 | Rowley . |
| 4,547,913 | 10/1985 | Phillips .................... 623/27 |
| 4,645,509 | 2/1987 | Poggi et al. ............. 623/55 |
| 5,004,477 | 4/1991 | Palfray ..................... 623/53 |
| 5,037,444 | 8/1991 | Phillips ..................... 623/55 |

FOREIGN PATENT DOCUMENTS

| | | | |
|---|---|---|---|
| 2640499 | 6/1990 | France ..................... 623/53 |
| 8909036 | 10/1989 | World Int. Prop. O. ........... 623/53 |

OTHER PUBLICATIONS

Burgess et al., Development and Preliminary Evaluation of the VA Seattle Foot, Journal of Rehabilitation Research & Development 22, 3, 75-84, Jul. 1985.

Primary Examiner—Randall L. Green
Assistant Examiner—David H. Willse
Attorney, Agent, or Firm—Pierre Lespérance

[57] ABSTRACT

An improved prosthetic foot keel is proposed, based on the capability of the flexible keel to maintain the amputee's stability by means of medio-lateral forces and impulsions, while initially storing energy at heel strike and mid-stance, for restoring same at toe-off, in all planes. The keel is of the cantilever spring type, as generally disclosed in U.S. Pat. No. 4,645,509 to Poggi et al.. The improvement is directed: firstly, to a medially-oriented heel curvature which, at heel strike, provides medio-lateral stability during the weight transfer from the contralateral limb to the prosthetic limb; and secondly, to an inward medio-lateral forefront portion extension thereof which, by extending the lever arm of the deformable keel, produces a medio-lateral propulsion capability at foot push off. Hence, this keel medio-lateral heel curvature and inward extension facilitates lateral back and forth swinging motion of the amputee's body center of gravity, typical of a normal gait.

6 Claims, 3 Drawing Sheets

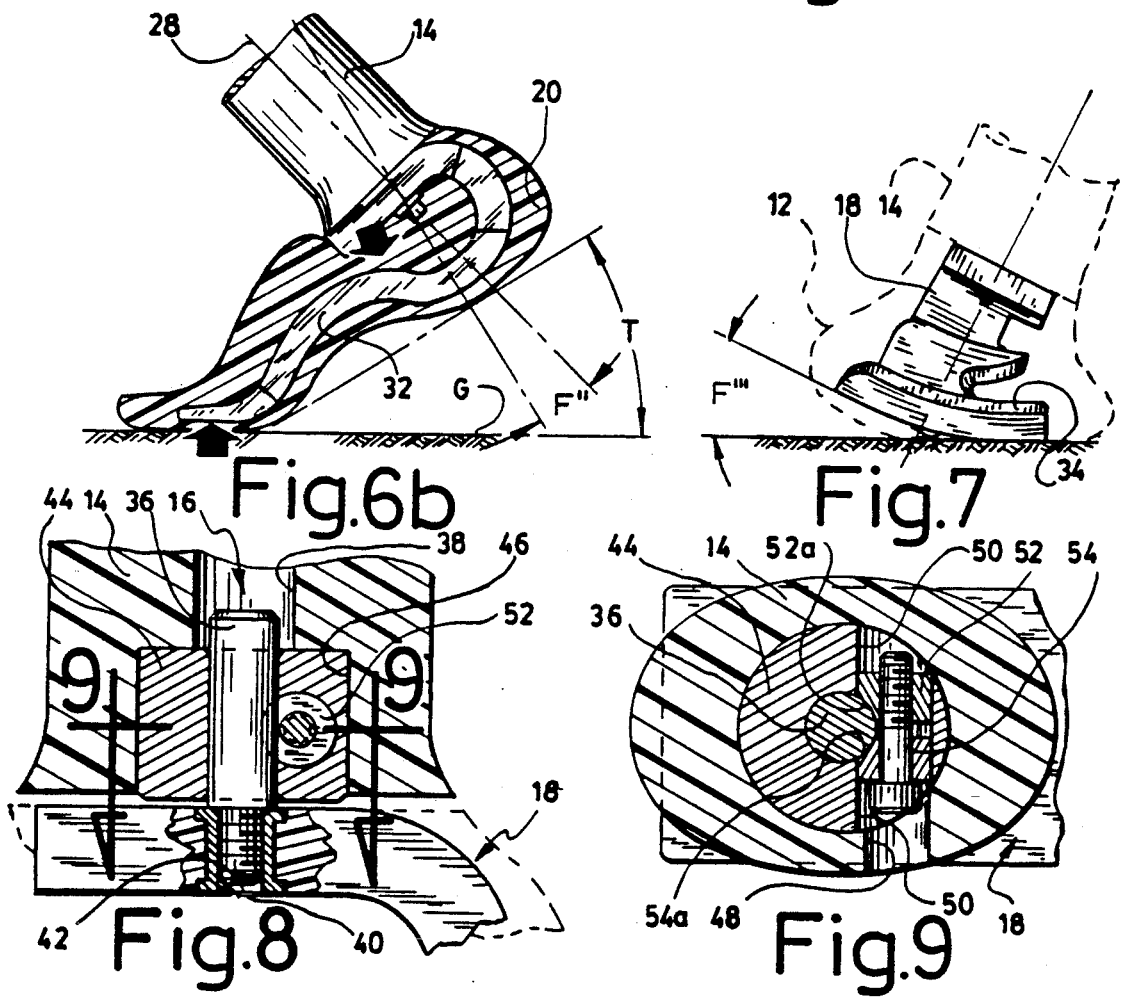

MEDIO-LATERAL CONTROL ENHANCING, CANTILEVER-SPRING TYPE PROSTHETIC FOOT

FIELD OF THE INVENTION

This invention relates to cantilever spring type, prosthetic feet capable of dynamically transforming heel strike deformation thereof, at foot-fall and mid-stance, into spring-back gait thrust, during toe-off.

BACKGROUND OF THE INVENTION

Below-knee or above-knee, leg amputated persons may nowadays regain some measure of locomotion autonomy by installing a prosthetic limb to their stump. The foot part of the prosthetic limb will usually be an add-on element to be fixedly yet releasably secured to the prosthetic leg part proper.

First generation prosthetic feet implements included feet articulated at the ankle, and others forming a rigid segment with the shank segment. These implements addressed the needs of amputees with respect to joint mobility or greater level of transportation autonomy.

Second generation prosthetic feet appeared as deformable foot frames or keels were provided, wherein the energy of deformation stored during heel strike (the foot heel initially engaging the ground) could be, at least in part, restored during the foot push-off period (just before foot rise), solely in the sagittal plane, in order to drive the artificial limb forward in the sagittal plane. Some of these second prosthetic feet are disclosed in the following United States patents:

(A) U.S. Pat. No. 4,547,913 issued on Oct. 22, 1985 to Flex Foot inc. (inventor V. Phillips).

(b) U.S. Pat. No. 4,645,509 issued on Feb. 24, 1987 to the Model & Instrument Development corp. (inventors: D. Poggi, E. Burgess, D. Moeller and D. Hittenberger)—the so-called "Seattle foot"—;

These prosthetic foot keels extend within a plane disclosing substantial symmetry with the lengthwise axis and sagittal plane of the prosthetic leg. The mechanical behaviour describing the deformation and energy storing and release of these second generation prosthetic feet have been well studied by those skilled in the art. Although these artificial feet were immediately heralded by users as a major improvement in comfort level, it was obvious from observations and results that walking cadence was still much lower and stride length, still far shorter than the natural cadence and stride length of unamputated persons. Such second generation implements could therefore be improved, to bring the amputee's gait more closely in line with unamputated person's gait.

Eventually, it became clear that inadequate medio-lateral control of the amputee's foot was at least in part to blame, i.e. the cyclic requirement of lateral back and forth swinging motions of the amputee's body center of weight from one leg to the other, during gait. Moreover, there was still too static or passive contribution of the prosthetic foot energy restoring, forward thrust capability at push-off (the "dead-leg" syndrome). Indeed, these artificial limbs did disclose at least fair to good forward and vertical push-off thrust capability, due to their spring-back capability and symmetrical shape about the sagittal plane of the leg, but the medio-lateral contribution was relatively limited. This is because for the latter to be achieved, it was required to pivot by internal rotation the whole foot about the substantially vertical, leg lengthwise axis, rather than through laterally inward roll motion of the prosthetic foot about its horizontal fore and aft axis, hingedly about the ankle, as is typically the case for healthy, full length, natural legs.

Moreover, it was recognized in the field that the much touted "Seattle foot", although efficient during athletic movements performed by the amputee, was much less advantageous for day to day normal walking. Indeed, it is recognized in the medical field that a majority of leg amputees, perhaps as much as 95% of them, can link their handicap to a prior, triggering vascular trauma usually associated with a heart attack. Such vascular trauma occurs overwhelmingly in the case of elderly patients, who normally would not engage into physically demanding sporting activities. The efficiency of the "Seattle foot" is low because, at slow cadence gait, the value of strained energy stored by keel flexion at heel strike, and following spring back energy restoration at toe-off, is typically only about 1.5 times the body weight of the amputee, whereas, at fast-cadence gait, said value is doubled to about 3 times the body weight of the amputee. Thus, spring back of the "Seattle foot" keel would be low if not negligible in the case of an elderly amputee, presenting very short stride lengths typical of a hesitant person who experiences trouble maintaining his stability over ground. Therefore, the "Seattle foot" for such amputees would not constitute an improvement over said first generation prosthetic limbs.

OBJECTS OF THE INVENTION

The gist of the invention is thus to provide a third generation prosthetic foot, aimed at improving the performance of the prosthetic foot generally disclosed in U.S. Pat. No. 4,645,509 issued in 1987 in the name of Poggi et al., notably with respect to overall stability of the walking amputee.

The general object of the invention is to improve ground stability confidence of below-knee or above-knee leg amputees fitted with a prosthetic foot.

A further object of the invention is to enable a leg amputee fitted with such a prosthetic foot, to safely increase his walking speed, including cadence and stride length by forwrad thrust, closer to the walking speeds of normal, unamputated persons, and to some extent also, to slightly reduce the time period of each gait cycle.

An important object of the invention is to provide such a prosthetic foot, which will substantially improve medio-lateral control of the prosthetic foot and amputee's body stability, during cyclic, back and forth weight transfer between the contra lateral leg during push-off, due to the sequential storing and relasing energy in the sagittal plane capability of the foot, while maintaining forward thrust and vertical propulsion.

Another important object of the prosthetic foot is to provide a cantilever spring keel capable of generating a three-axis pivot for toe-off energy release in all planes of the energy stored at heel-strike and mid-stance.

A general object of the invention is to enable both below-knee and above-knee leg amputees to more fully participate in demanding sporting activities requiring good lower limb propulsion, while remaining fully efficient for normal gait or even short to very short length stride, regular to slow cadence gait.

A corollary object of the invention is to improve gait symmetry between the natural leg and prosthetic leg of amputees.

SUMMARY OF THE INVENTION

Accordingly with the objects of the invention, there is disclosed an improved prosthetic foot keel, based on the capability of the flexible keel to maintain the amputee's stability by means of medio-lateral forces and impulsions, while initially storing energy at heel strike and mid-stance, for restoring same at toe-off, in all planes. The keel is of the cantilever spring type, as generally disclosed in U.S. Pat. No. 4,645,509 to Poggi et al.. The improvement is directed: firstly, to a medially-oriented heel curvature which, at heel strike, provides medio-lateral stability during the weight transfer from the contralateral limb to the prosthetic limb; and secondly, to an inward medio-lateral forefront portion extension thereof which, by extending the lever arm of the deformable keel, produces a medio-lateral propulsion capability at foot push off. Hence, this keel medio-lateral heel curvature and inward extension facilitates lateral back and forth swinging motion of the amputee's body center of gravity, typical of a normal gait.

More particularly, the invention concerns a keel for an amputee's prosthetic foot, comprising a cantilever spring monolithic member made of hardened polymer having visco-elastic properties, said cantilever spring member having: (a) an attachment means, adapted for connection to an upper prosthesis; (b) a forefoot portion; (c) an elongated curved heel portion, being a strain energy storing transition between said forefoot portion and said attachment means, said heel and forefoot portions being shaped for substantially uniform bending stress distribution and for storing strain energy throughout said cantilever spring member in reaction to each footfall and returning such energy as footlift and thrust with the following footrise; and (d) means for introducing medio-lateral stability at heel strike, during the weight transfer from the contralateral limb to said prosthetic foot, and for dynamically inducing, during prosthetic foot push-off immediately preceding footrise thereof, progressive medio-lateral inward weight transfer of the center of gravity of said amputee's body from said prosthetic foot toward the amputee's contra lateral limb.

Alternately, the invention relates to a cantilever spring type member for use by an amputee as the structural frame of a prosthetic foot, said cantilever frame having substantial rigidity and sturdiness yet being made from an elastic but resilient material; heel strike-induced deflection and foot pushoff induced springback, forward-thrust restoration of said spring type member operatively occurring during the cyclic loading/unloading of the prosthetic foot associated with gait footfall and toe-off of the prosthetic foot; and further including means cooperating with said cantilever member frame to introduce medio-lateral stability at heel strike during the weight transfer from the contra lateral limb to said prosthetic foot, and to dynamically induce a medio-lateral weight transfer of the center of gravity of said amputee body, from a position generally overlying said prosthetic foot, to a position generally overlying the amputee's contra lateral limb during prosthetic foot push-off immediately preceding toe-off of the prosthetic foot.

BRIEF DESCRIPTION OF THE DRAWINGS

FIGS. 6, 6a and 6b are vertical sectional views similar to FIG. 2 but at a reduced scale, suggesting the lengthwise flexing capability of the arched prosthetic foot keel in relation to various loads applied thereto;

FIG. 7 is a front end view of the prosthetic foot keel, taken from perspective 7 of FIG. 6a but with its polymeric encasement cover shown in dotted lines for clarity of the view, and suggesting the lateral flexing capability thereof;

FIG. 8 is an enlarged vertical section of one embodiment of the ankle connector means, for connecting the prosthetic foot keel to an associated prosthetic leg; and FIG. 9 is a downwardly looking cross-section along line 9—9 of FIG. 8.

DETAILED DESCRIPTION OF THE INVENTION

Figure 2:
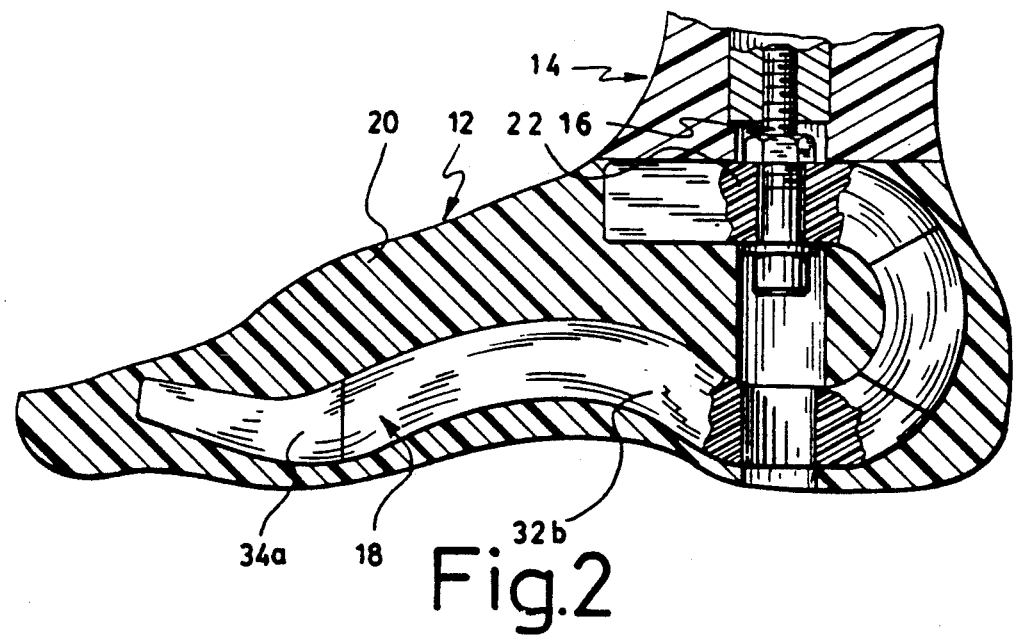
FIG. 2 is a vertical sectional view of the prosthetic foot, taken along line 2—2 of FIG. 1.
Figure 3:
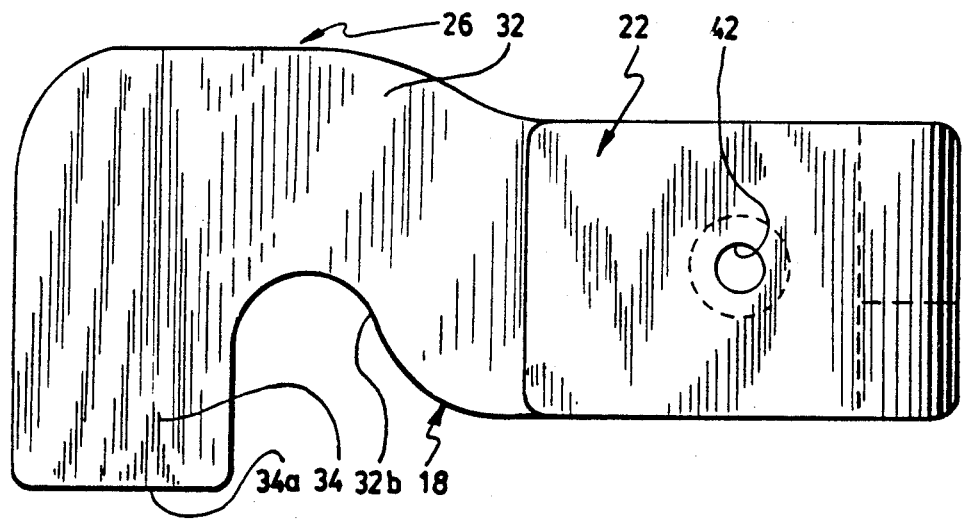
FIGS. 3–4 are a top plan view and a side elevational view respectively of the prosthetic foot keel, being in its operative upright, ground-standing position.
Figure 4:
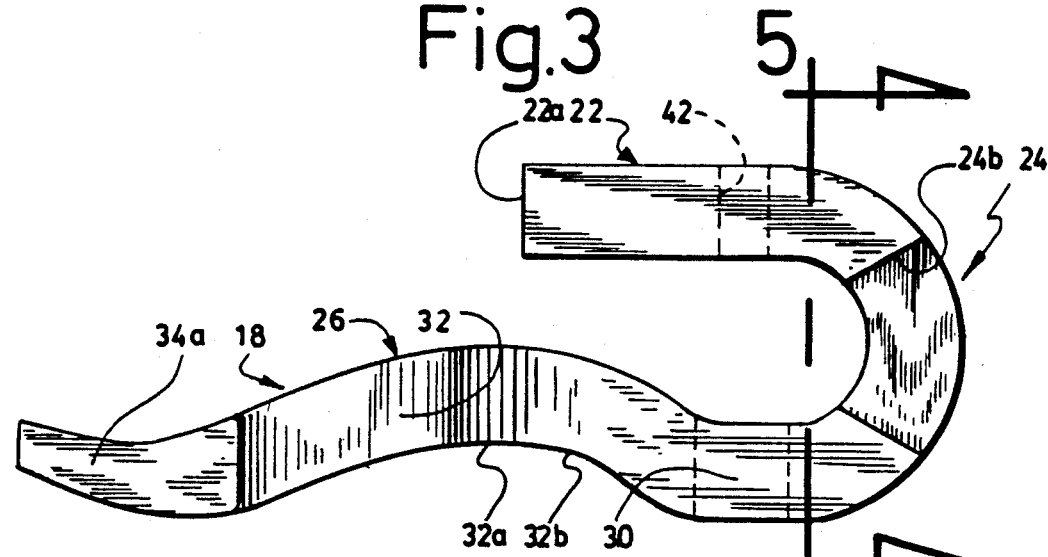

There is illustrated in FIG. 2 a prosthetic foot 12 and associated upper prosthetic leg 14, fixedly interconnected by connecting means 16. Artificial leg 14 is destined to be releasably fitted at its top end to the stump of the amputated leg of a handicapped person. The combination of prosthetic members 12, 14 with the amputated leg stump should be of a length commensurate with that of the other healthy leg, or of the normal foot for bilateral amputees.

Prosthetic foot 12 consists of a main frame or keel 18, and a full casing 20 into which is fully and firmly embedded frame 18. Preferably, casing 20 shapingly conforms to a healthy foot so as to simulate appearance of same, while frame 18 imparts substantial rigidity to the foot yet provides some measure of resilient elasticity to the foot 12 in the sagittal plane together with, as we will see below, in the medio-lateral direction, wherein three axis spatial control is introduced.

Keel 18 and cover 20 will each be made from a material chosen from the corresponding group outlined in U.S. Pat. No. 4,645,509 issued in 1987 in the name of Poggi et al. Thus, the material from which keel 18 will be made, and its particular shape, will be selected to provide a dampened spring effect, such that each footfall causes strain energy to be stored within the keel and then recovered in a timed spring-back or restoration that will complement the amputee's natural stride. The whole keel 18 will be of a single material construction, without seams or joints, preferably a hardened polymer disclosing resilient elasticity, for example the material under the DELRIN trademark. As for cover 20, it will preferably be made from a flexible cellular polymer, such as polyurethane.

Keel 18 forms an elongated, curve band and includes, in its operative, upright position illustrated in FIG. 2 where the artificial foot stands on the ground, an upper end ankle portion 22, an intermediate heel portion 24 and a forefoot end sole portion 26.

Upper end portion 22 engages the leg 14 fixedly releasably through the connector means 16. The forefoot end portion 26 is located opposite the ankle portion 22 and is destined to engage the ground indirectly through the thickness of the sole layer of polymeric cover material 20 therebeneath. Portions 22, 24, 26 form an integral, seamless, jointless keel 18.

Accordingly with the invention, and contrarily to the symmetrical shape of Poggi's prosthetic keel, the present invention keel 18 is not symmetric relative to the sagittal plane of the foot, i.e. has a medio-laterally irregular shape, as disclosed below. Keel upper ankle part 22 is preferably straight, flat, quadrangular in cross-section along its entire fore and aft length. By fore and aft is meant a direction parallel to the lengthwise axis of foot 12 which extends between the front foot "toes" 20a and the rear foot "heel" 20b of the artificial limb 12. The lengthwise fore and aft axis of ankle part 22 should be orthogonal to the lengthwise axis 28 (FIG. 6) of associated upper limb 14. The front end 22a of ankle part 22 is advantageously convexly laterally curved, to smooth out the edges.

The keel intermediate heel portion 24 is arcuate, extending for half a turn and integrally endwisely merging with the keel end portions 22 and 26.

Figure 1:
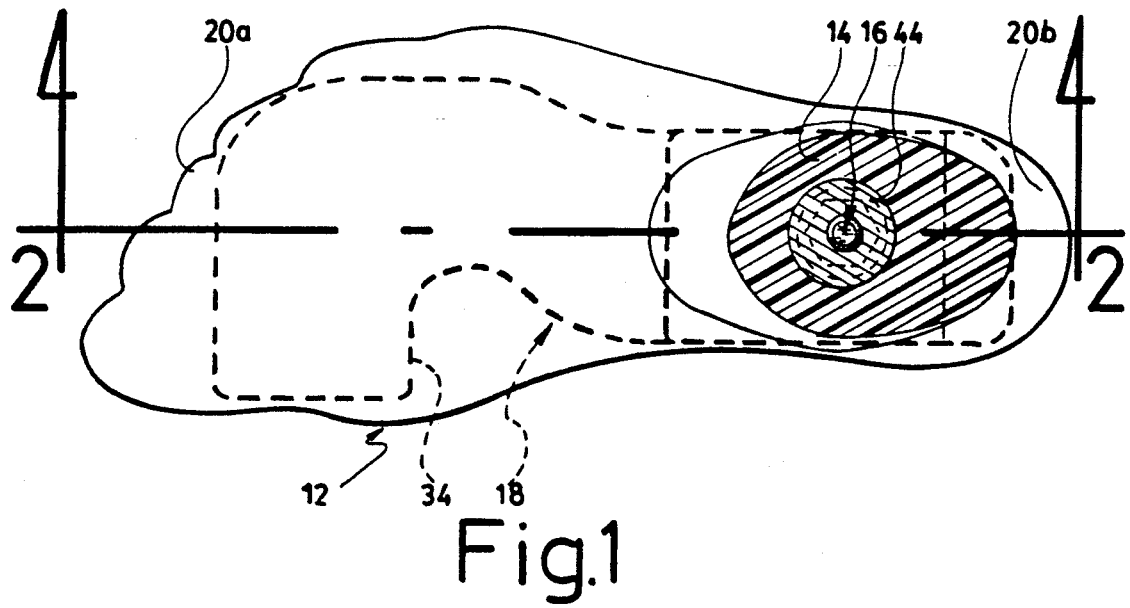
FIG. 1 is a downwardly looking, cross-sectional view of a prosthetic leg, showing in shadow outline a prosthetic right foot and in dotted lines the prosthetic foot keel constructed in accordance with the teachings of the invention.

Whereas ankle part 22 was straight and of substantially constant cross-section through its length, intermediate portion 24 has, accordingly with a critical feature of the invention, a variable cross-section which tapers outwardly medio-laterally relative to the sagittal plane, to define an outward, medio-lateral concavity. By "outward" is meant laterally outwardly of the foot 20, i.e. to the right of a right foot, as illustrated in FIGS. 1-2, or to the left of a left foot.

Figure 5:
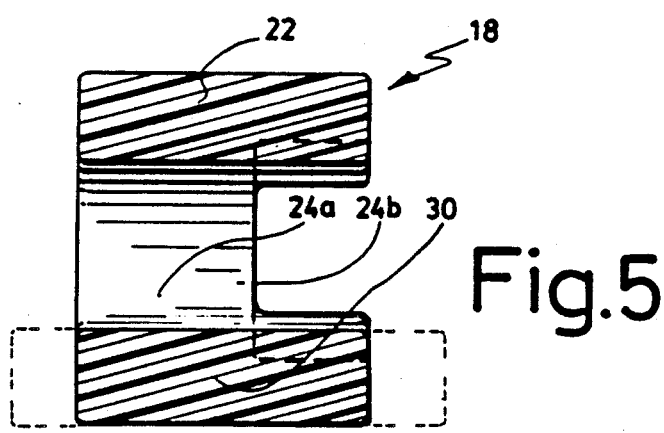
FIG. 5 is a cross-sectional view along line 5—5 of FIG. 4.

More specifically, and as clearly illustrated in FIG. 5, heel part 24 widthwisely tapers toward the intermediate section 24a of its length, so as to define a medially concave portion 24b as taken from an antero posterior direction. The curvature of medially concave portion 24b increases the moment arm between the ground and joint reaction forces. At heel-strike, the heel will bend, thereby medially controlling—i.e. resisting in part—the amputee's body weight transfer from the natural leg to the prosthetic leg. Therefore, this means that the contra-lateral limb can generate a greater and more efficient propelling force, since the prosthetic device can accommodate the induced thrust into deformation energy. Moreover, the antero-posterior medio-lateral concavity 24b of the keel heel portion 24 will also be able to absorb and resist or "brake" the medio-laterally outward force applied at the heel strike of the prosthetic foot by the contra lateral limb medio-laterally inward push-off. Indeed, the prosthetic limb capability of accommodating this induced force from the contra lateral limb in effect transform this medio-laterally outward force into deformation energy which will extend along the body of the prosthetic keel, thus dampening and eventually counteracting the medio-laterally outwardly directed force from the contra lateral limb (generally but not necessarily a natural leg) while recuperating this energy as stored deformation energy.

Preferably, heel part 24 remains substantially cross-sectionally constant in thickness.

Base or arch sole part 26 includes a short, straight, aft section 30, merging with the heel part 24 and in vertical axial register with ankle part 22 and with the upper limb main axis 28. Preferably, the laterally outward edges of keel portions 22 and 30, and the laterally outward edge 24a of the heel part intermediate section 24 being laterally outwardly shifted, are substantially coplanar i.e. symmetrical with the sagittal plane, as clearly shown in FIG. 5. Base part rear section 30 is preferably shorter in length than ankle part 22, but its overall length ultimately depends on the foot size of the handicapped person. Keel section 30 extends substantially parallel to ankle part 22.

Accordingly with an important although not critical feature of the invention, base part 26 further includes an intermediate, elongated, arcuate portion 32, integral to part 30. Arch 32 provides better energy absorbing capabilities at mid-stance, and improves the efficiency of spring back energy release at toe-off. This arch feature does not appear in the "Seattle foot" '509 patent, in which the keel forefront portion remains straight throughout.

The absolute length and extent of curvature of part 32 are again dependent upon the size of the handicapped person's foot, and at least to some extent, also upon the weight and height of that person. Portion 32 is upwardly curved, to define a bottom concave wall or arch 32a. Portion 32 should be thicknesswisely smaller than keel parts 22 or 24 or 30, and preferably be widthwisely intermediate parts 22 or 30 and part 24a. Moreover, arch part 32 is laterally outwardly deported beyond said common plane extending through the outer edges of keel parts 22, 24a and 30. Preferably, arch section 32 is substantially straight in a fore and aft, substantially constant quadrangular cross-section. Advantageously, aft portion 32b is widthwisely smaller than adjacent main portions 32a or part 30.

Accordingly with a fruther critical feature of the invention, base part 26 further includes a short transverse fore portion 34, integral to arch portion 32. Fore portion 34 must be made from same material as the rest of keel 18 and be integral thereto in a seamless, jointless fashion, wherein the flexing and resiliency features of all the keel portions will remain substantially the same along its length, for a given widthwise and thicknesswise dimension. Arch fore part 34 extends substantially coplanar to arch aft part 30, and transversely laterally inwardly of the fore and aft lengthwise axis of parts 30 and 32. By laterally inwardly is meant inwardly of the foot, i.e. leftwardly of a right foot (FIGS. 1-2) or rightwardly of a left foot.

Preferably, the lengthwise axis of fore part 34 is orthogonal to that of parts 22, 30 or 32. Preferably, part 34 is thicknesswisely substantially identical to arch part 32, but widthwisely intermediate heel section 24a and arch part 32. The free end 34a of toe part 34 could profitably be straight along a fore and aft vertical plane, or may have fore and aft rounded smooth edges. Said vertical plane extending through the part wall 34a should extend parallel to an laterally inwardly of the vertical plane extending through the laterally inward edges of keel parts 22 and 30.

Medially directed forefoot extension 34 operatively extends the lever arm, thereby producing a medio-lateral propulsion force at push-off, while forward and vertical thrust is maintained by the forefoot main arch body, 32, as well as by the arcuate heel portion 24.

FIGS. 6, 6a and 6b suggest that the deflection and restoration of the keel 18 under cyclic loading/unloading of footfall and toe-off, within the sagittal plane, sustains a substantially similar, timed or lagging stress versus yield relationship as the one disclosed in the patent to Poggi '509. That is to say, although there are many structural differences between the "Seattle foot", disclosed in the Poggi '509 patent and the present invention, notably with respect to the sagittal plane dissymmetry of the latter compared to the corresponding symmetry of the former, it is to be understood that the performance of the two keels are deemed by the present inventors as being substantially similar, when there is solely considered the deflection and restoration capabilities of the keel in the sagittal plane and the associated forward thrust typical of a straight, forwardly directed gait. These deflection and restoration capabilities of Poggi '509 were directed to the dynamic, rather than passive, interaction of the keel with the cyclic loading and unloading of the foot by the amputee's body motion, particularly in view of addressing the forward thrust needs necessary for athletic movements that the handicapped person wishes to be able to do.

FIG. 7 on the other hand clearly suggests the major improvement associated with the addition of the laterally inward, medio-lateral front keel extension 34, compared to the prior art keel and especially the '509 patent. Indeed, extension 34 forms an inward seat against which the load of the foot should come to bear, in a natural, comfortable gait, to be progressively applied at the intermediate step of the deflection portion of the keel flexing cycle following initial ground contact of the foot heel, and for the push-off step of the amputee's artificial leg upward and laterally inward, to swing the center of gravity of the amputee's body toward the contra lateral foot. Indeed, when the foot is being lifted to release the ground, the heel is lifted wherein the foot pivots on its toe portion (FIG. 6b). Of course, this cycle is repeated each time the ground-clearing artificial limb 12, 14 is lowered to the ground. This is because, in normal gait, there is continuous back and forth, lateral swinging displacement of the body's center of gravity over one and the other leg as each leg alternately engages the ground.

It is understood that the load applied on front seat 34 by the ground G will tiltingly deflect at least keel portion 32 along its lengthwise roll axis, as suggested in FIG. 7.

Such seat 34 improves the lateral stability of each footstep, without affecting the sagittal rebound or springback capability in the remaining portion 30-32 of the keel base that provided said forward thrust necessary for locomotion.

Thus, at heel strike, then at mid-foot stance, and finally at toe-off, upon lifting of the ground-engaging prosthetic foot, restoration of the flexed keel 18 occurs progressively with the toe seat 34 being last to release ground, as illustrated in FIG. 6b. Again, it is to be stressed as paramount that, as the prosthetic foot becomes airborne, the center of gravity of the amputee's body will be medially laterally inwardly swung toward a position substantially overlying the other, ground-engaging leg, (as part of the cyclical, back and forth, medio-lateral, natural swinging motion of the center of gravity during walking) so as not to transfer instability to the contra lateral foot, which has only slightly engage the ground in the walking sequence, and thus so as not to compromise overall stability of the walking handicapped person. This medio-lateral foot swing motion is made possible by the capability of the present prosthetic foot of pivoting about its lengthwise roll motion thanks to the laterally internally tiltable toe end 34 of the keel.

Furthermore, it was discovered that the forward thrust at push-off was improved due to the medio-lateral control afforded by toe end 34.

FIGS. 8-9 suggest one form of connector means 16. The specific type of connector means 16 is not critical, provided it provides substantially the same artificial limb anchoring performance as the "Seattle foot". In FIGS. 8-9, one example of such connector means 16 is shown to consist of a cylindrical stud 36, engaging the axial channel 38 of prosthetic leg 14. Stud 36 includes an axial threaded extension 40, threadedly engaging a threaded bore 42 transverse to keel part 22. Stud part 36 is releasably anchored to artificial leg 14 by a cylindrical block unit 44, engaging an enlarged countersunk channel portion 46 at the bottom end of channel 38 and coextensive therewith.

Cylindrical casings 14, 44 have each a radial through-bore 48, 50 registering with each other when block 44 is fully engaged into annular cavity 46 and suitably rotated to bring the two radial bores in respective register. Block 44 carries a first radial ear 52, extending radially outwardly transversely of channel 50, and a second radial ear 54, extending radially inwardly transversely of channel 50. Ears 52, 54 are spacedly opposite one another relative to shaft 36, as clearly illustrated in FIG. 9, and each includes a slanted, arcuate edge 52a, 54a frictionally engaging a peripheral section of shaft 36. Ear 52 has a transverse through-bore. Hence, engagement of ears 52, 54 by a bolt will tightingly anchor shaft 36 to block 44. Block 44 may be welded in position within annular cavity 46.

It was discovered that the present resilient keel, compared to Poggi'"Seattle foot" keel, enables a 15% increase in natural walking speed resulting from a 7% increase in cadence and 8% increase in stride length, together with a 34% increase in the foot push-off force and 47% medial braking force occuring during inward lateral weight transfer from the prosthetic leg. Confidence with the new design developed quickly for the amputees fitted experimentally with the present device. Gait symmetry between the natural leg and prosthetic leg of amputees was found to be substantially improved, albeit not totally restored as it can exist with two natural legs.

Preferably, a cushion heel (not illustrated) is added to foot 12, anchored to the polyurethane encasement 20 about the aft sole portion thereof, in register with keel portion 30. This cushion heel would help in dissipating frictional energy associated with walking and in dampening the impact from heel strike on the ground.

It is understood that, although the keel 18 was detailed for use with a right foot, another keel (not shown) being a mirror-image of keel 18 is envisioned to be used for a left foot. Such a left foot keel would be well within the scope of the present invention.

I claim:

1. A prosthetic foot keel consisting of a cantilever spring monolithic member made from a substantially rigid, yet resiliently elastic material, and forming a generally rectangular band defining one an another lateral side edges; said band formed of three integral parts, namely:

(a) a C-shape heel part, at one end of said band, said heel part consisting of a straight, free, outer end portion, an opposite, straight, inner end portion substantially parallel to said outer end portion, and an arcuate portion integrally joining said inner and outer end portions; said arcuate portion itself defining an intermediate transverse cavity made into said one lateral side edge at said arcuate portion; said heel part free end portion further having attachment means for connection to an upper prosthesis;

(b) a forefoot part, at the end of said band opposite said heel part, a flange projecting transversely from said another lateral side edge at said forefoot part integrally thereto; and (c) a curved part, integrally interconnecting said forefoot part and said heel part inner end portion, said curved part curved toward a plane intersecting said heel part free end portion, whereby said heel part, forefoot part and curved part extend substantially within a single sagittal plane, and said forefoot flange projecting outwardly from and about an axis orthogonal to said sagittal plane; wherein upon said cantilever spring member being fitted to an amputee's limb through said attachment means, said cantilever spring member, during gait, will absorb energy at said heel part during prosthetic foot heel strike, will store said energy, will transfer this stored energy to said curved part and forefoot part, and will restore said energy at foot push-off in such a way as to provide substantial medio-lateral control of the prosthetic foot during both loading and unloading of the prosthetic foot keel.

2. A prosthetic foot keel as defined in claim 1, wherein the thickness of said forefoot part and integral flange tapers toward the end of said band opposite said heel part.

3. A prosthetic foot keel as defined in claim 2, wherein said curved part further defines a second transverse cavity, made into said another lateral side edge at an intermediate portion thereof proximate said flange.

4. A prosthetic foot keel as in in claim 3, wherein said heel part inner end portion is substantially shorter than said heel part free outer end portion, whereby the latter extends spacely over part of said curved part.

5. A prosthetic foot keel as in claim 4, wherein the least width of said band is defined about said arcuate portion intermediate cavity.

6. A prosthetic foot keel as in claim 5, wherein the combination of said forefoot part and flange defines the greatest width of said band.

* * * * *